(12) United States Patent
Burzynski et al.

(10) Patent No.: US 6,372,938 B1
(45) Date of Patent: Apr. 16, 2002

(54) SYNTHESIS OF 4-PHENYLBUTYRIC ACID

(75) Inventors: Stanislaw R. Burzynski, 20 W. Rivercrest, Houston, TX (US) 77042; Leszek Musial, Stafford, TX (US)

(73) Assignee: Stanislaw R. Burzynski, Houston, TX (US)

( * ) Notice: Subject to any disclaimer, the term of this patent is extended or adjusted under 35 U.S.C. 154(b) by 52 days.

(21) Appl. No.: 09/862,074

(22) Filed: May 21, 2001

(51) Int. Cl.$^7$ .............................................. C07L 53/134
(52) U.S. Cl. ........................................ 562/496; 562/465
(58) Field of Search ................................... 562/496, 465

(56) References Cited

U.S. PATENT DOCUMENTS 6,037,376 A    3/2000    Samid

OTHER PUBLICATIONS

Ohkawa, S. Terao, S., Terashita, Z., Shibouta, Y., Nishikawa, K., "Dual Inhibitors of Thromboxane A2 Synthase and 5–Lipxygenase with Scavenging Activity of Active Oxygen Species. Synthesis of a Novel Series of (3–Pyridyl-methyl)benzoquinone Derivatives", 1991, 267–281.

Primary Examiner—Paul J. Killos
(74) Attorney, Agent, or Firm—Howrey Simon Arnold & White, LLP

(57) ABSTRACT

A method of synthesizing compounds of Formula I:

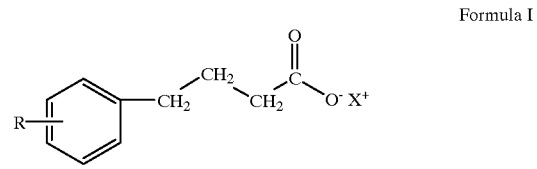

Formula I by reacting aromatic compounds with butyrolactone, followed by neutralization with base. The reaction can be conducted in the presence of a catalyst. Preferred catalysts are Lewis acids. A preferred product of Formula I is 4-phenylbutyric acid, which is obtained by the reaction of benzene with butyrolactone in the presence of aluminum chloride, followed by neutralization with base.

20 Claims, No Drawings

SYNTHESIS OF 4-PHENYLBUTYRIC ACID

BACKGROUND OF THE INVENTION

This invention relates to a novel synthetic approach to compounds of Formula I.

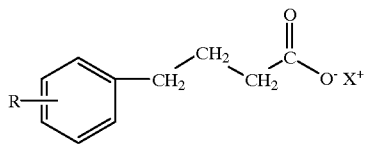

Formula I

Phenylbutyric acid and its pharmaceutically acceptable derivatives are particularly preferred targets of the present invention. Sodium phenylbutyrate has been used extensively for the treatment of urea cycle disorders (Batshaw et al., Brusilow et al. (*Ped. Research*), Brusilow et al. (*New Eng. J. Med.*), Finkelstein et al., Maestri et al., Redonnet-Vernhet et al., Rowe et al.). Phenylbutyrate derivatives have also shown promising pharmaceutical properties in the treatment of sickle cell anemia (Collins et al., Dover et al. (*New Eng. J. Med.*), Dover et al. (*Blood*)). cystic fibrosis (Bradbury et al., Loffing et al.), AIDS (Roberts et al.), and several types of cancer (Carducci et al., Darmanun et al., Englehard et al., Gorospe et al.).

In the past, phenylbutyrate derivatives have been prepared by the Arndt-Einstert reaction, using diazomethane with silver oxide and sodium thiosulfate (*J. Chem. Soc.*, 1997–99 (1938)). Alternatively, thianapthene-2-acetic acid and thianapthene-3-acetic acid have been used to prepare β-phenylbutyric acid (*J. Am. Chem. Soc.*, 70, 3768 (1948)). The Gignard reagent, benzyl magnesium chloride, has also been used in the synthesis of phenylbutyric acid, resulting in a yield of 16.1% (*J. Am. Chem. Soc.*, 71, 2807–2808 (1949)).

It would be advantageous to have a synthetic route to phenylbutyrate and derivatives thereof that is not hindered by the synthetic restrictions, i.e., the necessity to vigorously exclude moisture from diazomethane and Grignard reagents, and that would give higher yields of product than the reactions described above.

SUMMARY OF THE INVENTION

One aspect of the present invention is a method of preparing a compound of Formula I:

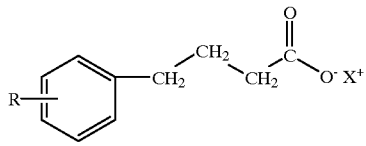

Formula I wherein R is independently selected from hydrogen, halo, C1–C4 alkyl, alkenyl, alkynyl, C3–C6 cycloalkyl, C1–C4 alkoxy, alkenoxy, alkynoxy; and X is hydrogen, an alkali metal cation, an ammonium or a substituted ammonium. According to one embodiment of the invention, the method comprises the steps of, a) reacting a compound of Formula II;

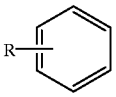

Formula II wherein R is as defined above, with a compound of Formula III; and

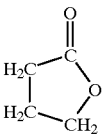

Formula III b) reacting the resulting compound with a compound of Formula IV;

Formula IV where X is as defined above, and Z is hydroxy, sulfate, phosphate, bicarbonate, carbonate, or alkoxy, and b and c are independently 1–5. A particularly suitable compound of Formula IV is sodium hydroxide.

According to one aspect of the invention the reaction of a compound of Formula I with the compound of Formula II is conducted in the presence of a catalyst. Particularly suitable catalysts are Lewis acids, including, but not limited to aluminum chloride, zinc chloride, iron chloride, stannous chloride, boron tribromide, boron trifluoride, or sulfuric acid.

A particular aspect of the present invention is a method of preparing a 4-phenylbutyric acid by reacting benzene with butyrolactone.

DETAILED DESCRIPTION OF THE INVENTION

It will be recognized by one skilled in the art based on the following description and illustrative examples that the present invention is a method of synthesizing compounds of Formula I:

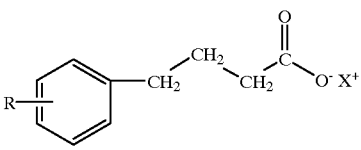

Formula I wherein R is independently selected from hydrogen, halo, C1–C4 alkyl, alkenyl, alkynyl, C3–C6 cycloalkyl, C1–C4 alkoxy, alkenoxy, alkynoxy; and X is hydrogen, an alkali metal cation, an ammonium or a substituted ammonium.

It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The method of the present invention comprises the steps of a) reacting a compound of Formula II;

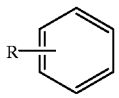

Formula II with a compound of Formula III.

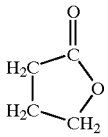

Formula III

A particularly preferred compound of Formula II is benzene. According to one embodiment of the present invention, the reaction is conducted in a solvent. According to an alternative embodiment, the compound of Formula II is itself the solvent for the reaction.

A catalyst may be used to facilitate the reaction of the compound of Formula II with the compound of Formula III. One preferred class of catalysts is Lewis acids. Examples of particularly preferred catalysts are aluminum chloride, zinc chloride, iron chloride, stannous chloride, boron tribromide, boron trifluoride, and sulfuric acid.

According to one embodiment of the invention, the catalyst is added to a mixture of a compound of Formula II and an appropriate solvent or to neat compound of Formula II, if no solvent is used. This mixture is maintained, preferably with stirring, at a temperature between about −80° C. and the boiling point of the solvent at ambient pressure. Preferably the mixture is maintained between 0° C. and the boiling point of the solvent. The mixture of a compound of Formula II and catalyst can be stirred for a time ranging from several seconds to several days before a compound of Formula III is added to the mixture. Preferably, the mixture of a compound of Formula II and catalyst is stirred for a time ranging from about 1 min to about 30 min before a compound of Formula III is added.

The compound of Formula III can be added to the mixture of a compound of Formula II and catalyst as a neat reagent, or can be added as a solution in an appropriate solvent. The compound of Formula III is added dropwise, in small aliquots, or as a large portion. Subsequent to the complete addition of a compound of Formula III, the reaction mixture is maintained, preferably with stirring, at a temperature between about −80° C. and the boiling point of the solvent at ambient pressure. Preferably the mixture is maintained between 0° C. and the boiling point of the solvent. The reaction mixture can be so maintained for a time ranging from a few seconds to about 24 hr. Preferably, the reaction mixture is maintained about 10 min to about 180 min, more preferably from about 60 min to about 120 min.

The reaction mixture can be quenched via the addition of a quenching agent. Suitable quenching agents are of Formula IV:

$$X_b—Z_c$$ Formula IV where X is as defined above, and Z is hydroxy, sulfate, phosphate, bicarbonate, carbonate, or alkoxy, and b and c are independently 1–5. Quenching agent can be added neat or as a solution in an appropriate solvent. A particularly preferable quenching agent is an aqueous solution of base. A preferred base is sodium hydroxide. Another preferred quenching agent is a mixture of a solution of aqueous base and ice.

The quenched solution can be maintained at a temperature from about 0 to about 50° C. for a time ranging from a few minutes to about 10 hr, preferably from about 1 hr to about 3 hr. The pH of the solution can be maintained from about 6.5 to about 10, preferably from about 9 to about 9.5. The pH of the solution can be further raised by the addition of base. The quenched solution can be purified by filtration to remove any particulate that can be present. The quenched solution can be further purified by contacting it with an organic solvent to extract remaining starting materials, side products, and impurities. Examples of suitable extraction solvents include chloroform, dichloromethane, trichloromethane, carbontetrachloride, and diethyl ether. The product can be precipitated from the aqueous solution by the addition of acid. The product can be isolated by filtration, or extracted into a suitable organic solvent. If the product is extracted into an organic solvent, it can be recovered upon evaporation of the solvent.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Powdered aluminum chloride (200 g) was added to benzene (400 g) and stirred for 10 min at 50° C. Butyrolactone (86 g) was added in small portions. The temperature was maintained between 50 and 60° C. for 90 min and then the reaction mixture was added, with stirring, to a mixture of ice and 5% sodium hydroxide. The temperature was maintained below 35° C. and the pH was maintained between 9 and 9.5 for 2 hr. The mixture was filtered under vacuum. Phenylbutyric acid was precipitated from the aqueous fraction by the addition of ice and hydrochloric acid. Crude (93.7%–94.3%) 4-phenylbutyric acid was isolated by vacuum filtration.

Crude 4-phenylbutyric acid was purified by vacuum distillation (120–125° C., 1 mm Hg). The acid was dissolved in 5% sodium hydroxide and agitated. The acid was dissolved in 5% sodium hydroxide and agitated with carbon tetrachloride for 15 minutes. Carbon tetrachloride was removed and the 4-phenylbutyric solution was mixed with acetone, methanol and a small amount of activated charcoal for 15 minutes at ambient temperature. The mixture was filtered and acidified by the addition of HCl. Crystals of 4-phenylbutyric acid (81.15% yield) were isolated and dried by lyophilization. HPLC analysis indicates 99.87% purity of the final product.

All of the methods disclosed and claimed herein can be made and executed without undue experimentation in light of the present disclosure. While the compositions and methods of this invention have been described in terms of preferred embodiments, it will be apparent to those of skill in the art that variations can be applied to the methods and in the steps or in the sequence of steps of the method described herein without departing from the concept, spirit and scope of the invention. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Carducci M. A., Nelson J., Chan-Tack K., Ayyagari S. R., Sweatt W., Campbell P., Nelson W., Simons J. Phenylbutyrate Induces Apoptosis in Human Prostate Cancer Therapy and is More Potent than Phenylacetate. Podium Presentation, American Urological Association, Las Vegas, Nev. April, 1995. *Clinical Cancer Research* 2: 379–387. 1996.

Darmanun D., Welch S., Rini A., et al Phenylbutyrate-induced Glutamine Depletion in Humans: Effect on Leucine Metabolism. *Am J Physiol* 274(5 Pt 1): E801–7. May 1998.

Englehard H., Homer R. J., Duncan H., Rozental J. Inhibitory Effects of Phenylbutyrate on the Proliferation, Morphology, Migration and Invasiveness of Malignant Glioma Cells. *J. Neuro-Oncology.* 37:97–108. 1998.

Roberts J, McGregor W. G. Inhibition of Mouse Retroviral Disease by Bioactive Glutaminase-asparaginase *J. Gen. Virol.* 72: 299–305. 1991.

Bradbury N. A., Focus on "Sodium 4-phenylbutyrate Downregulates Hsc70: Implications for Intracellular Trafficking of DF508-CFTR." *Am J Physiol Cell Physiol* 278(2) :C257–8. February 2000.

Loffing J., Moyer B. D., Reynolds D., Stanton B. A., PBA Increases CFTR Expression but at High Doses Inhibits Cl(−) Secretion in Calu-3 Airway Epithelial Cells. *Am J. Physiol* 277(4 Pt 1):L700–8. October 1999.

Collins A. F., Pearson H. A., Giardina P., McDonagh K T., Brusilow S W., Dover G. J. Oral Sodium Phenylbutyrate Therapy in Homozygous b Thalassemia: A Clinical Trial. *Blood.* 85: 43–49. 1995.

Dover D., Brusilow S., Samid D. Increased Fetal Hemoglobin in Patients Receiving Sodium 4-Phenylbutyrate. *New Eng. J. Med.* 327:569–570, Oct. 1, 1992.

Dover G. J., Brusilow, S., Charache S., Induction of Fetal Hemoglobin Production in Subjects with Sickle Cell Anemia by Oral Sodium Phenylbutyrate. *Blood.* 184(1) :339–43. July 1994.

Brusilow S. Phenylacetylglutamine May Replace Urea as a Vehicle for Waste Nitrogen Excretion. Ped. Research. 29(2):147–150. 1991.

Brusilow S., Danney M., Waber L., Batshaw M., et al. Treatment of Episodic Hyperammonemia in Children with Inborn Errors of Urea Synthesis. *New Eng. J. Med.* 310:1630–34. June 1984.

Finkelstein J. E., Hauser E. R., Leonard C. O., Brusilow S. W. Late-onset Ornithine Transcarbamylase Deficiency in Male Patients. *J Ped.* 117(6):897–902. 1990.

Maestri N., Hauser E., Bartholomew D., Brusilow S. Prospective Treatment of Urea Cycle Disorders. *J Ped.* 119(6):923–928. 1991.

Redonnet-Vernhet I., Rouanet F., Pedespan J M, Hocke, C., Parrot F., A Successful Pregnancy in a Heterozygote for OTC Deficiency Treated with Sodium Phenylbutyrate. *Neurology.* 54(4):1008. Feburary 2000.

Rowe P., Newman S., Brusilow S. Natural History of Symptomatic Partial Omithine Transcarbamylase Deficiency. *New Eng. J. Med.* 314:541–547. 1986.

We claim:

1. A method of preparing a compound of Formula I:

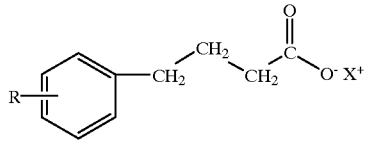

Formula I wherein
R is independently selected from hydrogen, halo, C1–C4 alkyl, alkenyl, alkynyl, C3–C6 cycloalkyl, C1–C4 alkoxy, alkenoxy, alkynoxy; and
X is hydrogen, an alkali metal cation, an ammonium or a substituted ammonium;
the method comprising;
a) reacting a compound of Formula II;

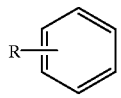

Formula II wherein R is as defined above, with a compound of Formula III; and

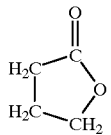

Formula III b) reacting the resulting compound with a compound of Formula IV;

$X_b$—$Z_c$  Formula IV where X is as defined above, and Z is hydroxy, sulfate, phosphate, or alkoxy, bicarbonate, carbonate and b and c are independently 1–5.

2. The method according to claim 1, wherein the compound of Formula IV is sodium hydroxide.

3. The method according to claim 1, wherein all R are hydrogen.

4. The method of claim 1, wherein the reaction of the compound of Formula I with the compound of Formula II is in the presence of a catalyst.

5. The method of claim 4, wherein the catalyst is a Lewis acid.

6. The method of claim 5, wherein the catalyst is aluminum chloride, zinc chloride, iron chloride, stannous chloride, boron tribromide, boron trifluoride, or sulfuric acid.

7. The method of claim 6, wherein the catalyst is aluminum chloride.

8. The method of claim 7, wherein a mixture comprising the compound of Formula II and aluminum chloride are stirred together for about 10 min at a temperature between about 40° C. and about 60° C., followed by the addition of the compound of Formula III.

9. The method of claim 8, wherein the compound of Formula III is stirred with the mixture comprising the compound of Formula II and aluminum chloride for about 90 min at a temperature between about 50° C. and about 60° C., followed by the addition of sodium hydroxide.

10. A method of preparing a 4-phenylbutyric acid comprising;
   a) reacting benzene with butyrolactone; and
   b) reacting the resulting mixture with a compound of $X_b$—$Z_c$, wherein X is hydrogen, an alkali metal cation, an ammonium or a substituted ammonium; Z is hydroxy, sulfate, phosphate, or alkoxy, bicarbonate, carbonate and b and c are independently 1–5.

11. The method of claim 10, wherein the reaction of benzene with butyrolactone is in the presence of a catalyst.

12. The method of claim 11, wherein the catalyst is a Lewis acid.

13. The method of claim 12, wherein the catalyst is aluminum chloride, zinc chloride, iron chloride, stannous chloride, boron tribromide, boron trifluoride, or sulfuric acid.

14. The method of claim 13, wherein the catalyst is added to the benzene prior to the reaction with butyrolactone to yield a mixture of benzene and catalyst.

15. The method of claim 14, wherein the mixture of benzene and catalyst is stirred together for 1 min to about 15 min prior to the reaction with butyrolactone.

16. The method of claim 15, wherein the mixture of benzene and catalyst is stirred at a temperature between about 50° C. and about 60° C. prior to the addition of butyrolactone.

17. The method of claim 14, wherein the butyrolactone is added to the mixture of benzene and catalyst to yield a reaction mixture comprising benzene, catalyst, and butyrolactone.

18. The method of claim 17, wherein the reaction mixture comprising benzene, catalyst and butyrolactone is stirred for 30 min to about 120 min.

19. The method of claim 18, wherein the reaction mixture comprising benzene, catalyst and butyrolactone is maintained between 50° C. and about 60° C.

20. The method of claim 19, further comprising the steps of:
   c) quenching the reaction mixture comprising benzene, catalyst and butyrolactone with and aqueous mixture comprising a compound of Formula IV,
   d) contacting the combined aqueous mixture and reaction mixture with an organic solvent to yield an organic phase and an aqueous phase,
   e) adding acid to the aqueous phase to lower the pH of the aqueous phase by an amount sufficient to precipitate product from the aqueous phase, and
   f) separating the product from the aqueous phase.

* * * * *

UNITED STATES PATENT AND TRADEMARK OFFICE
CERTIFICATE OF CORRECTION

PATENT NO. : 6,372,938 B1  Page 1 of 1
APPLICATION NO. : 09/862074
DATED : April 16, 2002
INVENTOR(S) : Stanislaw R. Burzynski and Leszek Musial It is certified that error appears in the above-identified patent and that said Letters Patent is hereby corrected as shown below:

Column 6, line 53:   delete "Formula I" insert --Formula II--

Column 6, line 53:   delete "Formula II" insert --Formula III--

Signed and Sealed this

Eleventh Day of November, 2008

JON W. DUDAS
*Director of the United States Patent and Trademark Office*